United States Patent [19]

Nelson

[11] Patent Number: 4,711,965
[45] Date of Patent: Dec. 8, 1987

[54] PREPARATION OF ALKYL SILANES

[75] Inventor: Gunner E. Nelson, Baton Rouge, La.

[73] Assignee: Ethyl Corporation, Richmond, Va.

[21] Appl. No.: 17,852

[22] Filed: Feb. 24, 1987

[51] Int. Cl.$^4$ ................................................ C07F 7/08
[52] U.S. Cl. ................................................... 556/478
[58] Field of Search ....................................... 556/478

[56] References Cited

U.S. PATENT DOCUMENTS

| | | | |
|---|---|---|---|
| 2,857,414 | 10/1958 | Schmidt et al. | 556/478 X |
| 3,103,526 | 9/1963 | Jenkner | 556/478 X |
| 3,398,171 | 8/1968 | Giraitis et al. | 556/478 |
| 3,480,654 | 11/1969 | Sundermeyer et al. | 556/478 X |
| 4,367,343 | 1/1983 | Tamborski et al. | 556/478 X |
| 4,595,777 | 6/1986 | Bakshi et al. | 556/478 |

FOREIGN PATENT DOCUMENTS 825987 12/1959 United Kingdom ................ 556/478
900132 7/1962 United Kingdom ................ 556/478

OTHER PUBLICATIONS

Tamborski et al, Ind. Eng. Chem. Prod. Res. Dev. 22, 172-178 (1973).

*Primary Examiner*—Paul F. Shaver
*Attorney, Agent, or Firm*—Donald L. Johnson; John F. Sieberth; Robert A. Linn

[57] ABSTRACT

Alkali metal aluminates, NaAlR$'_4$, react with alkyl trihalosilanes, RSiX$_3$, in accordance with the following equation:

$$0.75 \ NaAlR'_4 + RSiX_3 \rightarrow RSiR'_3 + 0.75 \ NaAlX_4 \qquad (1)$$

The process is conducted at elevated temperature. Products of the process are useful as functional fluids.

6 Claims, No Drawings

PREPARATION OF ALKYL SILANES

FIELD OF THE INVENTION

This invention relates to the reaction of alkali metal aluminum tetraalkyls (also known as alkali metal aluminates) with alkyl halosilanes. The invention also pertains to use of the alkylsilane products as functional fluids.

RELATED ART

Methods for the synthesis of tetraalkyl silanes include the reaction of alkyl magnesium halides or alkyl lithiums with halosilicon compounds; Tamborski et al U.S. Pat. No. 4,367,343, and Tamborski et al, Synthesis and Properties of Silahydrocarbons, A Class of Thermally Stable, Wide Liquid Range Fluids, *Ind. Eng. Chem. Prod. Res. Dev.* 22 172–178 (1983).

British Pat. No. 825,987 to Kali-Chemie AG discloses the reaction of trialkyl aluminums with alkyl- or aryl-chlorosilanes.

Jenkner, British patent No. 900,132, (also to Kali-Chemie) pertains to the reaction of sodium aluminum tetraethyl with halosilanes, such as silicon tetrachloride, where the reactants are used in a ratio of 4 to 1.

Bakshi et al. U.S. Pat. No. 4,595,777 pertains to the process of reacting an alkylchlorosilane with a trialkylaluminum.

Giraitis et al, U.S. Pat. No. 3,398,171, relates to the reaction of organosilanes and mixed metal compounds $AMR_n$ wherein A is an alkali metal and M can be aluminum. The process is conducted at a reaction temperature of $-20°$ C. to $+50°$ C. and uses a higher mole ratio of reactants than utilized in this invention (compare the paragraph bridging Columns 5 and 6 of the reference patent with the description of this invention given below).

SUMMARY OF THE INVENTION

This invention pertains to the preparation of tetraalkylsilanes, wherein one alkyl group is comparatively small and the other three are comparatively large. The small alkyl group has from one to about four carbon atoms, while the larger three groups have from about 8 to about 14 carbon atoms each. These products are prepared by a process which comprises reacting an alkali metal aluminum tetraalkyl, $MAlR'_4$, with an alkyl trihalosilane, $RSiX_3$, wherein X is a halide group and R is the smaller alkyl group (one to about four carbons). The process is conducted such that about 3 to about 4 moles of metal tetraalkyl are reacted with each 4 mole portion of alkyl trihalosilane employed.

More particularly, in the process of this invention three moles of $MAlR'_4$ reactant combine with four moles of alkyltrihalosilane reactant. In order to assist the reaction through the effect of mass action, an excess of up to about one additional mole of $MAlR'_4$ can be utilized in the reaction mixture. For the process of this invention, one does not use a very large excess of $MAlR'_4$ reactant, since such excesses can cause the reaction to take a different course that for the purpose of this invention is not desired; cf, Jenkner, and Giraitis et al, supra.

Although not bound by any theory, it is believed the process of this invention can be represented by the following equation:

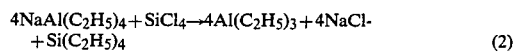

$$0.75\ NaAlR'_4 + RSiX_3 \rightarrow RSiR'_3 + 0.75\ NaAlX_4 \qquad (1)$$

In a preferred embodiment, R is methyl and X is chloride, so that a preferred reactant is methyltrichlorosilane, $CH_3SiCl_3$.

The process of this invention has several key features. First, all alkyl groups in the metal aluminate reactant $MAlR'_4$ (except for those in the excess reactant employed) are utilized. Second, it is not necessary for purposes of economics to recycle alkyl aluminum values. Recycle of such compounds is very difficult (if not impossible) to accomplish at an acceptable cost, especially when the alkyl groups are of the preferred size for this invention ($C_8$–$C_{14}$). Third, when a trichlorosilane such as $CH_3SiCl_3$ is used as a reactant in the process of this invention, co-product $NaAlCl_4$ separates as a separate liquid phase. Fourth, this facilitates product workup. Fifth, the product of this invention is predominately the fully substituted product. Hence, the process of this invention is much more advantageous than the Bakshi method (U.S. Pat. No. 4,595,777 supra, in which a mixture of products occur.

Above it was stated that a key feature of this invention was the utilization of the alkyl groups in the $MAlR'_4$ reactant. Perhaps this can be better understood if the process of this invention is contrasted with processes of the prior art. In this regard the process of Jenkner (British No. 900,132) can be depicted by the following equation:

$$4NaAl(C_2H_5)_4 + SiCl_4 \rightarrow 4Al(C_2H_5)_3 + 4NaCl + Si(C_2H_5)_4 \qquad (2)$$

As can be seen, most of the alkyl groups in the product remain bonded to aluminum, hence the Jenkner process is not as efficient as applicants for transferring alkyl groups from aluminum to silicon. Also, a pertinent aspect of the Giraitis et al process can be represented by the following equation:

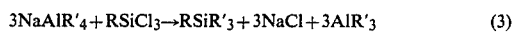

$$3NaAlR'_4 + RSiCl_3 \rightarrow RSiR'_3 + 3NaCl + 3AlR'_3 \qquad (3)$$

Here again, most of the alkyl groups in the product mixture remain bonded to aluminum. Therefore, these prior art processes are much less efficient than the process of this invention. Therefore, the process of this invention represents a decided improvement in the art.

In the alkali metal aluminum tetraalkyls ($MAlR'_4$) used as reactants in the process of this invention, the organic radicals need not be the same. To prepare a reactant with dissimilar groups, one may react, for example, a metal aluminum hydride such as $NaAlH_4$ or $LiAlH_4$ with a mixture of olefins (such as a mixture of octene-1 and decene-1). This reaction may be conducted in accordance with the general procedure for preparing $MAlR'_4$ starting materials given below. Alternatively, one may use in the process of this invention a mixture of two or more metal aluminates wherein each one is prepared from a single olefin. Hence, in this invention there can be used, for example, a mixture of two aluminates such as $NaAl(C_8H_{17})_4$ and $NaAl(C_{10}H_{21})_4$. The ability to use a mixture of alkyl radicals as exemplified above is important, since a mixture can be chosen to produce a silane product with desired physical properties.

In many instances where a mixture of alkyl groups occurs within the metal aluminate starting material, the products obtained by the process of this invention are substantially in the calculated statistical ratios. For example, reaction of CH$_3$SiCl$_3$ with NaAl(C$_8$H$_{17}$)$_2$(C$_{10}$H$_{21}$)$_2$ yields a mixture of products, CH$_3$Si(C$_8$H$_{17}$)$_3$, CH$_3$Si(C$_8$H$_{17}$)$_2$(C$_{10}$H$_{21}$), CH$_3$Si(C$_8$H$_{17}$)(C$_{10}$H$_{21}$)$_2$, and CH$_3$Si(C$_{10}$H$_{21}$)$_3$ in a relative mole quantity that approximates 0.125, 0.375, 0.375, 0.125, as predicted for random distribution.

Products of this invention are useful as functional fluids with such diverse suggested uses as engine lubrication, electrical insulation, and heat transfer media. They can also be used as hydraulic fluids. The products of this invention are particularly useful under high temperature conditions where petroleum-based or synthetic hydrocarbon-based fluids cannot meet specifications. Product mixtures can be made to achieve desired rheological properties.

DESCRIPTION OF PREFERRED EMBODIMENTS

In a highly preferred embodiment this invention comprises a process for the preparation of a tetralkylsilane,

wherein R and R' represent alkyl radicals such that R has up to about 4 carbon atoms, and the radicals represented by R' are alike or different and have from about 8 to about 14 carbon atoms; said process comprising reacting (a) an alkali metal aluminum tetraalkyl MAlR'$_4$, wherein M is Li, Na or K, and the radicals represented by R' are alike or different, and (b) a trihaloalkyl silane having the formula RSiX$_3$, wherein X is a halide radical, preferably selected from fluoride, chloride and bromide radicals, said process being conducted such that the mole ratio of reactant (a) to reactant (b) is substantially 0.75 to 1, to 1.0 to 1.0.

As stated above, the process of this invention comprises a reaction of an alkali metal aluminate, MAlR'$_4$. Lithium, sodium and potassium aluminates can be used, with the lithium and sodium compounds being preferred. The sodium aluminates are highly preferred for reasons of economics and availability. Preferably, each radical indicated by R', in the formula MAlR'$_4$ is a hydrocarbyl, straight chain alkyl radical of about 8 to about 14 carbon atoms; however, it is to be understood that the radicals need not be limited to this structural configuration, and the size of the radicals can be larger or smaller than those within the preferred range.

The radicals of the preferred configuration and size appear to yield the more useful products, and they are preferred for that reason. However, any metal aluminate MAlR'$_4$ can be used for the process of this invention, so long as the radicals depicted by R' are stable under the reaction conditions employed, do not form an untoward amount of undesirable co-product when subjected to the reaction conditions employed, or unduly retard the reaction because of steric hindrance.

As mentioned above, the metal aluminate reactant may contain one or more groups indicated by R'. Alternatively, a mixture of metal aluminates can be used. The metal aluminate or aluminates need not be pure; for example, an aluminate can be used in the reaction mixture in which it is formed. Thus for example, Na, Al, and H$_2$ can be reacted in a hydrocarbon to form NaAlH$_4$ and the unisolated NaAlH$_4$ can be reacted with an olefin, such as octene-1, or a mixture of olefins, such as octene-1 and decene-1 in a mole ratio of 2 to 1, and the resultant reaction mixture used as a reactant in the process of this invention. When the reactant is formed in this way, the olefin is generally used in excess. Consequently, the reactant mixture used in the instant process can frequently contain an olefin, or mixture of olefins.

Most olefins available in large commercial quantities are made from natural products or by chain growth of ethylene. In either case, the olefin usually has an even number of carbon atoms. However, it is to be understood that an even number of carbon atoms is not critical, and MAlR'$_4$ reactants with one or more R' radicals having an odd number of carbon atoms can also be used in this invention. Nevertheless, because of the more ready availability of even numbered olefins, the preferred MAlR'$_4$ reactants for this invention have alkyl radicals (depicted by R') that are derived from one or more of the following olefins:

octene-1
decene-1
dodecene-1
tetradecene-1
hexadecene-1

The other reactant employed in the process of this invention is an alkyl trihalosilane, RSiX$_3$. In this reactant, R is a lower alkyl radical such as methyl, ethyl, propyl, butyl, isopropyl, sec-butyl or the like. Preferably, R is unbranched. More preferably, R is methyl. The three groups indicated by X are halide radicals; preferably all three are the same; however, reactants with two or three halo groups per molecule can be used. More preferably, the halide groups are chloro or bromo radicals, most preferably they are all chloro groups.

The process of this invention is conducted using a temperature that is high enough to cause the reaction to take place at a reasonable rate, but not so high that it causes an undesirable amount of side reaction or decomposition to occur. Generally speaking, a temperature above 150° C. and below 230° C. is used. Preferably, the temperature is from about 180° C. to 200° C.

The reaction time is not a truly independent variable but depends at least to some extent on the other reaction conditions employed such as the reaction temperature. Generally speaking, reaction is essentially complete in from about 3 to 10 hours with 5 to 6 hours being typical.

The reaction pressure does not have a large effect on the course of the reaction. Atmospheric, sub-atmospheric and super atmospheric pressure can be used. Atmospheric pressure or the autogenous pressure of the system are preferred.

Although the process of this invention is preferably conducted using alkali metal aluminates, MAlR'$_4$, such as described above, it is to be borne in mind that similar reactants can also be used in this invention in substantially the same way, to produce substantially the same results. Thus for example, one may use alkaline earth aluminates, M'(AlR'$_4$)$_2$, wherein M' is Mg, Ca or Ba. When these materials are used in the process of this invention, one-half of the molar quantities described above for MAlR'$_4$ reactants are employed, since each molecule of the alkaline earth compounds contains two, i.e. twice, as many (AlR'$_4$) groups. One may use as a reactant a compound having the formula R"SiX$_3$ wherein R" is an alkyl group that has 5 or more carbon atoms.

GENERAL PROCEDURE

(A) Preparation of tetralkylaluminate reactant

Lithium aluminum hydride reacts with olefins at about 110°–120° C. forming complexes with the structure $LiAlR_4$. Sodium aluminum hydride is not added to olefins even at 180° C. without the presence of catalytic amounts of a material selected from trialkyl aluminums, dialkyl aluminum hydrides, lithium aluminum hydride, or aluminum, zinc or lithium halide. The first three hydrogens are readily replaced at 80°–130° C., but the fourth requires a temperature of 170°–230° C. or thereabouts, for about 3 to 6 hours. The process is preferentially conducted in the presence of an excess of olefin, e.g. a 1:8 mole ratio of $NaAlH_4$ to olefin, and 5–15 mole % (based on $NaAlH_4$) of the catalyst. A parafin diluent can be used in the reaction mixture.

As an illustration of the preparation of $NaAlR'_4$, a reactor is charged with $NaAlH_4$, catalyst, and olefin in the above-defined relative amounts and heated for 1–2 hours at 125° C., followed by 3–4 hours at 175° C. (It is believed the duration of the heating cycle can be reduced somewhat.) The product is discharged after cooling. The final product typically contains 30–65% of $NaAlR_4$, and is suitable for most reactions. It is not necessary that the aluminate be employed in the product mix; if desired it can be isolated from some or all of the other substances present in the resultant reaction mixture.

The following illustrates how to conduct the process of this invention. A reaction mixture is prepared by admixing a sodium aluminum tetraalkyl solution prepared as above, and methyl trichlorosilane. The mole ratio of contained $NaAlR'_4$ to $CH_3SiCl_3$ is equal to or substantially equal to 0.75 to 1.0 to 1.0 to 1.0. The reaction mass is heated to about 190° C. for 2–6 hours, with efficient stirring.

Product workup is conducted as follows:

Sodium aluminum hydride is added (to reduce any unreacted $CH_3SiCl_3$ to $CH_3SiH_3$) and the resultant mixture stirred for about 3 hours at room temperature. In this step, any $CH_3SiH_3$ formed is evolved as a gas.

The mixture is then hydrolyzed with 3N HCl to remove any hydride remaining. The organic phase (which contains the product) is separated and dried. The products of this invention may contain, in addition to the desired tetraalkyl silane some olefin dimer and/or some $RSiR'_2H$ by-product.

The above-described product workup can be conducted by two related, alternative procedures. As described above, the entire reaction product can be utilized in the workup. This method is convenient for small scale, laboratory preparations. Alternatively, before product workup, the $NaAlCl_4$ (or analogous coproduct) can be separated from the organic layer. In this alternative method, the workup procedure is conducted on the organic fraction after separation of the inorganic co-product. Preferably, the inorganic coproduct is removed as a liquid while it is in a molten state. Generally speaking, the process of this invention is conducted above the melting point of $NaAlCl_4$ coproduct; and therefore, the co-product can be discharged in a molten state from the reaction vessel, and then separated from the remainder of the product mixture. This is the preferred procedure for larger scale preparations.

The treatment of the reaction mixture with sodium aluminum hydride is utilized to facilitate analysis of the product mixture. Therefore, it does not comprise an essential part of the process, and it is not necessary to include this step in the workup of the reaction mixture.

EXAMPLE 1

This reaction was conducted in substantial accordance with the general procedure set forth above for preparing the products of this invention. There was used, 45.6 millimoles of sodium aluminum tetraoctyl and 57.3 millimoles of methyl trichlorosilane (mole ratio 0.80 to 1.0). The aluminum compound was in a 35% solution in octene-1. The reaction temperature and time were 190° C. and 5 hours. The product mixture was treated with 10 millimoles of sodium aluminum hydride (in 4 milliliters of dimethoxyethane solution) and stirred for three hours at room temperature. The product yield by gas chromatographic (GC) analysis was:

| | |
|---|---|
| $CH_3Si(C_8H_{17})_2H$ | 5.5% |
| $CH_3Si(C_8H_{17})_3$ | 77.1%, 75.7% |

The average of the duplicate analysis reported above is 76.4%. These results are based on silicon charged.

This yield and product composition compares very favorably to a reaction conducted at 90° C. for 2 hours using 37.2 mmoles of $NaAl(C_8H_{17})_4$ and 36.2 millimoles of $CH_3SiCl_3$; mole ratio 1.03 to 1. In that instance the product yield by GC was as follows:

| | |
|---|---|
| $CH_3Si(C_8H_{17})_3$ | 42.5% |
| $CH_3Si(C_8H_{17})_2H$ | 37.0% |
| $CH_3Si(C_8H_{17})H_2$ | 12.1% |
| | 91.6% closure on Si |

The process of this example can be extended to the use of lithium and potassium aluminum tetraalkyls in which the alkyl groups are octyl, decyl, dodecyl or tetradecyl. Such substances may be reacted with methyl, ethyl, n-propyl, isopropyl, or n-butyl trichlorosilane or the trifluoro or tribromo analogs of these substances. The reaction can be conducted at exogenous pressure or at pressures of up to 500 psi or higher, imposed by use of an inert gas atmosphere, e.g. nitrogen or argon. The reactions can be conducted at 180° C. to 230° C. for 3 to 10 hours. The mole ratio of metal aluminate to trihalosilane is in the range of about (0.75–1.0) to 1.0.

EXAMPLE 2

This procedure was conducted in general accordance with the procedure described above using 43.1 millimoles of $NaAl(C_8H_{17})_4$, 42.3 millimoles of KCl, and 40.4 millimoles of $CH_3SiCl_3$. The aluminum compound was used as a 45.3% solution in octene-1, and the mole ratio of the aluminate to halosilane was (43.1/40.4), i.e. 1.07 to 1. The reactants were contacted at 190° C. for 5 hours. The product mixture was hydrolyzed with 50 mL of 3N HCl, washed with 50 mL of 3N HCl, and then 50 mL of $H_2O$. The organic liquid was dried and evaporated to 59.3 grams.

Analysis (GC) indicated a 102% yield of $CH_3Si(C_8H_{17})_3$ was obtained. Although the analysis obviously comprised some analytical difficulty, the process of this example is an indication that the method of this invention can be conducted in the presence of a metal halide. Later work substantiated this, but also indicated that metal halides do not substantially enhance the process of this invention. In fact as shown below, their presence may be deleterious.

EXAMPLE 3

An 89.6% yield of $CH_3Si(C_8H_{17})_3$ was obtained by reacting 81.9 millimoles of sodium aluminum tetraoctyl as a 40% solution in octene-1 with 79.7 millimoles of $CH_3SiCl_3$. Heating the reaction mixture was conducted while stirring; 100° C. for 1 hour and then at 190° C. for 5 hours. The reaction procedure and product workup were in general accordance with the previous description.

In another run, a 92.5% yield of $CH_3Si(C_8H_{17})_3$ was obtained by reacting 60 millimoles of crude $NaAl(C_8H_{17})_4$ with 58 millimoles of $CH_3SiCl_3$ by stirring and heating at 100°–125° C. for 1 hour, followed by 5 hours at 190° C.

The product workup was in the usual manner. A black scum was noted at the interface of the organic and inorganic phases. The black scum is believed to be titanium. Titanium was present in the aluminum that was reacted with sodium and hydrogen to form the $NaAlH_4$, which in turn was reacted without purification or isolation to produce the $NaAl(C_8H_{17})_4$ reactant that was used in this experiment. The results indicate that workup of the $NaAlH_4$ intermediate, or the $NaAlR'_4$ reactant produced therefrom, is not required. Stated another way, good results are obtained when isolation techniques are not used to isolate the $NaAlH_4$ precursor, or the $NaAlR'_4$ reactant from other substances present in the reaction mixtures in which they are produced.

EXAMPLE 4

A mixture of 63.9 millimoles of $NaAl(C_8H_{17})_2(C_{10}H_{21})_2$ and 61.2 millimoles of $CH_3SiCl_3$ was reacted in a manner similar to the general procedure described above. The product contained a mixture of the following:

|  | Millimoles |
| --- | --- |
| $CH_3Si(C_8H_{17})_3$ | 5.38 |
| $CH_3Si(C_8H_{17})_2(C_{10}H_{21})$ | 17.11 |
| $CH_3Si(C_8H_{17})(C_{10}H_{21})_2$ | 17.11 |
| $CH_3Si(C_{10}H_{21})_3$ | 5.81 |

In another reaction, a mixture of 48.3 millimoles of $NaAl(C_8H_{17})_2(C_{10}H_{21})_2$ and 62.7 millimoles of $CH_3SiCl_3$ (mole ratio 0.77 to 1.0) was reacted similarly to above. The product distribution had essentially the same pattern, total yield, 81.6%. It was noted that less olefin dimerization occurred when the relative amount of $NaAlR^1_2R^2_2$ was reduced (from 1/2.2 to 1/6 dimer to product by weight).

In a third reaction, the above procedure was repeated using 51.6 millimoles of sodium aluminum tetraoctyl and 66.8 millimoles of $CH_3SiCl_3$; (mole ratio 0.77 to 1.0) and 53.3 millimoles of KCl. Stirring was conducted while the reaction was heated at 120° C. for 1 hour and at 190° C. for 5 hours. During the process, heavy solid deposition occurred making the stirring ineffective. Results were as follows:

|  | Yield |
| --- | --- |
| $CH_3Si(C_8H_{17})H_2$ | 33% |
| $CH_3Si(C_8H_{17})_2H$ | 30.5% |
| $CH_3Si(C_8H_{17})_3$ | 11.6% |

This result indicates that the reactants must be well contacted by efficient stirring, or by some other means.

In a fourth reaction, an 81.2% total yield of $NaAlR_4$ was prepared by reacting 41.8 millimoles of $NaAl(C_{10}H_{21})_4$, 43.0 millimoles of $NaAl(C_8H_{17})_4$ and 104 millimoles of $CH_3SiCl_3$. The Al/Si ratio was 0.815. Reaction in the usual manner was conducted (1 hour at 25° C. followed by 5 hours at 190° C.). The product mix was as follows:

|  | Mole % |
| --- | --- |
| $CH_3Si(C_8H_{17})_3$ | 14.2 |
| $CH_3Si(C_8H_{17})_2(C_{10}H_{21})$ | 37.7 |
| $CH_3Si(C_8H_{17})(C_{10}H_{21})_2$ | 37.7 |
| $CH_3Si(C_{10}H_{21})_3$ | 12.5 |

This distribution is about the same as noted for reactions previously described above. Thus, the product distribution appears to be substantially insensitive to aluminate composition and to Al/Si ratios over the (0.75 to 1.0) to (1.0 to 1.0) range.

EXAMPLE 5

Following the general procedure noted above, the following were reacted for 1 hour at 125°0 C. and then 5 hours at 190° C.:

32.6 millimoles $NaAl(C_{10}H_{21})_4$
65.0 millimoles $NaAl(C_8H_{17})_4$
100.0 millimoles $CH_3SiCl_3$
The $C_8$ to $C_{10}$ mole ratio was about 2 to 1.

The product yield was 87.45% and had the following distribution:

|  | Millimoles |
| --- | --- |
| $CH_3Si(C_8H_{17})_3$ | 26.91 |
| $CH_3Si(C_8H_{17})_2(C_{10}H_{21})$ | 38.46 |
| $CH_3Si(C_8H_{17})(C_{10}H_{21})_2$ | 18.85 |
| $CH_3Si(C_{10}H_{21})_3$ | 3.23 |

The olefin dimer to product ration was 1/6.

In another run, when 48.7 millimoles of $NaAl(C_{10}H_{21})_4$ and 80.2 millimoles of $NaAl(C_8H_{17})_4$ were reacted with 160.5 millimoles of $CH_3SiCl_3$, the product distribution was:

|  | Mole % |
| --- | --- |
| $CH_3Si(C_8H_{17})_3$ | 25.0 |
| $CH_3Si(C_8H_{17})_2(C_{10}H_{21})$ | 43.3 |
| $CH_3Si(C_8H_{17})(C_{10}H_{21})_2$ | 25.9 |
| $CH_3Si(C_{10}H_{21})_3$ | 5.8 |

The products of this invention are useful as functional fluids. For example, samples of materials of this invention were prepared by the above procedure, such that the $C_8$ to $C_{10}$ mole ratio was as indicated in the left hand column in the following table. The viscosity measurements reported in the table were obtained on the products. The results indicate that at least two of the three silacarbon mixtures compare favorably with U.S. Air Force synthetic lube specifications:

Viscosity of CH$_3$Si(Octyl)$_n$(Decyl)$_{3-n}$ Preparations

|  | Centistokes | | |
| --- | --- | --- | --- |
|  | −54° C. | 38° C. | 204.0 C. |
| Air Force Specification | 2500 max | 9.5 min | 0.9 min |
| Preparations |  |  |  |
| C$_8$/C$_{10}$ mole ratios |  |  |  |
| 2/1 | 2160 | 9.55 | 0.92 |
| 1.6/1 | 2290 | 9.90 | 0.93 |
| 1/1 | 2560 | 10.4 | 0.97 |

Products of this invention are useful as hydraulic fluids for military or other applications. Hydraulic fluids are used in hydraulic systems to transmit pressure or energy. They also serve to reduce friction in bearings and between sliding surfaces in pumps and similar articles. Hydraulic and other functional fluids also protect surfaces from rusting, and can remove undesirable particulate matter away from surfaces.

Like other functional fluid base stocks, the silahydrocarbons produced by the process of this invention can be admixed with additives such as rust inhibitors, antiwear agents, corrosion inhibitors and the like.

It is to be understood that modification of the above described invention can be made without departing from the spirit and scope of the following claims.

I claim:

1. Process for the preparation of a tetralkylsilane having the formula:

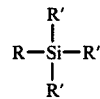

wherein R and R' alkyl radicals and the radicals R' are alike or different, such that R has up to about 4 carbon atoms, and each radical designated by R' has from about 8 to about 14 carbon atoms; said process comprising contacting reactants (a) and (b) wherein:

(a) is an alkali metal aluminum tetraalkyl having the formula MAlR'$_4$, wherein M is lithium, sodium, or potassium, and R' has the same significance as above, and (b) is an alkyltrihalosilane having the formula RSiX$_3$, wherein X is a halide radical selected from fluoride, chloride and bromide, and R has the same significance as above;

said process being conducted such that the mole ratio of reactant (a) to reactant (b) is from about 0.75 to 1.0, to about 1 to 1, and the reaction temperature is from about 180° C. to about 230° C.

2. A process of claim 1 wherein said alkali metal aluminum tetraalkyl has the formula NaAlR'$_4$ wherein the four alkyl radicals represented by R' are the same.

3. A process of claim 1 wherein said alkali metal aluminum tetraalkyl is a sodium aluminum tetraalkyl wherein the R groups are C$_8$ and C$_{10}$ alkyl radicals and wherein the mole ratio of C$_8$ to C$_{10}$ radicals is about 2:1.

4. A process of claim 1 wherein said reactant (b) is methyl trichlorosilane.

5. A process of claim 1 wherein said reaction temperature is above about 160° C.

6. A process of claim 5 being further characterized in that molten NaAlCl$_4$ co-product of said process is separated from the fraction of the reaction mixture containing said RSiR'$_3$ product.

* * * * *

UNITED STATES PATENT AND TRADEMARK OFFICE
CERTIFICATE OF CORRECTION

PATENT NO. : 4,711,965

DATED : December 8, 1987

INVENTOR(S) : GUNNER E. NELSON

Page 1 of 2

It is certified that error appears in the above-identified patent and that said Letters Patent is hereby corrected as shown below:

Column 1, line 18 reads "Dev. 22 172-178" and should read -- Dev. 22, 172-178 --.

Column 1, line 64 reads "supra." and should read -- supra. --.

Column 2, line 21 reads "(U.S. Pat. No. 4,595,777 supra," and should read -- (U.S. Pat. No. 4,595,777 supra, --.

Column 3, lines 5 and 6 read "relatiVe" and should read -- relative --.

Column 3, line 68 reads "H2" and should read -- $H_2$ --.

Column 4, line 29 reads "sec-butyl" and should read -- sec-butyl --.

Column 5, line 49 reads "produot" and should read -- product --.

Column 6, line 26 reads "at 90°C." and should read -- at 190°C. --.

Column 6, line 40 reads "n-propyl, isopropyl, or n-butyl" and should read -- n-propyl, isopropyl, or n-butyl --.

Column 7, after line 47 insert -- Total Yield was 74.2% --.

Column 8, line 14 reads "25°C." and should read -- 125°C. --

Column 8, line 33 reads "125°0C." and should read -- 125°C. --.

Column 8, line 48 reads "ration" and should read -- ratio --.

UNITED STATES PATENT AND TRADEMARK OFFICE
CERTIFICATE OF CORRECTION

PATENT NO. : 4,711,965
DATED : December 8, 1987
INVENTOR(S) : GUNNER E. NELSON

It is certified that error appears in the above-identified patent and that said Letters Patent is hereby corrected as shown below:

Column 10, line 7 reads "R' alkyl" and should read
-- R' are alkyl --.

Signed and Sealed this

Second Day of August, 1988

Attest:

DONALD J. QUIGG

Attesting Officer

Commissioner of Patents and Trademarks